(12) United States Patent
Weinberg

(10) Patent No.: US 11,298,103 B2
(45) Date of Patent: Apr. 12, 2022

(54) FLUID FLOW ANALYSIS

(71) Applicant: IMPERIAL COLLEGE INNOVATIONS LIMITED, London (GB)

(72) Inventor: Peter David Weinberg, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 432 days.

(21) Appl. No.: 16/087,442

(22) PCT Filed: Mar. 17, 2017

(86) PCT No.: PCT/GB2017/050749
§ 371 (c)(1),
(2) Date: Sep. 21, 2018

(87) PCT Pub. No.: WO2017/163030
PCT Pub. Date: Sep. 28, 2017

(65) Prior Publication Data
US 2019/0099153 A1    Apr. 4, 2019

(30) Foreign Application Priority Data

Mar. 22, 2016 (GB) ...................................... 1604873

(51) Int. Cl.
*A61B 8/06* (2006.01)
*A61B 8/08* (2006.01)
(Continued)

(52) U.S. Cl.
CPC ................ *A61B 8/06* (2013.01); *A61B 5/026* (2013.01); *A61B 5/0285* (2013.01);
(Continued)

(58) Field of Classification Search
CPC ....... A61B 8/06; A61B 8/0891; A61B 8/5223; A51B 5/026; A51B 5/0285; A51B 5/1075;
(Continued)

(56) References Cited

U.S. PATENT DOCUMENTS

| | | | |
|---|---|---|---|
| 4,637,401 A | 1/1987 | Johnston | |
| 5,383,369 A | 1/1995 | Khuri-Yakub et al. | |

(Continued)

FOREIGN PATENT DOCUMENTS

| | | | |
|---|---|---|---|
| CN | 1559345 A | 1/2005 | |
| CN | 101779967 A | 7/2010 | |

(Continued)

OTHER PUBLICATIONS

Ye Li, "Propagation and Reflection of Pulse Wave in Flexible Tubes and Relation to Wall Properties", Dec. 2011, Brunel Institute for Bioengineering Brunel University, pp. 1-202 (Year: 2011).*

(Continued)

*Primary Examiner* — Boniface Ngathi
(74) *Attorney, Agent, or Firm* — Marshall, Gerstein & Borun LLP

(57) ABSTRACT

A method of determining a measure of wave speed or intensity in a fluid conduit uses ultrasound measurements to determine the conduit diameter and fluid velocity in a volume element, each as a function of time, and each at a same longitudinal position of the conduit. The ultrasound measurement to determine fluid velocity is effected by tracking objects within the fluid flow in successive frames sampling the volume element, and obtaining displacement vectors for the objects. A wave speed may be determined from a ratio of the change in fluid velocity at the longitudinal position as a function of time and the change in a logarithmic function of the conduit diameter as a function of time. A (Continued)

measure of wave intensity may be determined as a function of change in determined conduit diameter and corresponding change in fluid velocity.

26 Claims, 3 Drawing Sheets

(51) Int. Cl.
| | |
|---|---|
| G01F 1/72 | (2006.01) |
| G01P 5/24 | (2006.01) |
| G01F 1/708 | (2006.01) |
| A61B 5/026 | (2006.01) |
| G01F 1/66 | (2006.01) |
| A61B 5/107 | (2006.01) |
| A61B 5/0285 | (2006.01) |
| G01F 1/7082 | (2022.01) |
| G01F 1/667 | (2022.01) |

(52) U.S. Cl.
CPC .......... *A61B 5/1075* (2013.01); *A61B 8/5223* (2013.01); *G01F 1/66* (2013.01); *G01F 1/667* (2013.01); *G01F 1/7082* (2013.01); *G01F 1/72* (2013.01); *G01P 5/245* (2013.01); *A61B 8/0891* (2013.01)

(58) Field of Classification Search
CPC .......... G01F 1/66; G01F 1/667; G01F 1/7082; G01F 1/72; G01P 5/245; G16H 50/30
See application file for complete search history.

(56) References Cited

U.S. PATENT DOCUMENTS

| | | |
|---|---|---|
| 6,682,483 B1 | 1/2004 | Abend et al. |
| 2005/0070798 A1 | 3/2005 | Pedrizzetti et al. |
| 2010/0113930 A1 | 5/2010 | Miyachi |
| 2012/0283564 A1 | 11/2012 | Ebbini et al. |
| 2014/0276072 A1 | 9/2014 | Martins et al. |

FOREIGN PATENT DOCUMENTS

| | | |
|---|---|---|
| CN | 102905614 A | 1/2013 |
| EP | 0595666 A2 | 5/1994 |
| WO | WO-97/24986 A2 | 7/1997 |
| WO | WO-2008/008936 A2 | 1/2008 |
| WO | WO-2011/110817 A2 | 9/2011 |
| WO | WO-2015/013196 A2 | 1/2015 |
| WO | WO-2015/026787 A2 | 2/2015 |

OTHER PUBLICATIONS

Lingli Liu et al, "Development of a custom-designed echo particle image velocimetry system for multi-component hemodynamic measurements: system characterization and initial experimental results", Phys. Med. Biol. 53 (2008) 1397-1412 (Year: 2008).*
Office Action issued in Chinese Patent Application No. 201780029789.5 dated Sep. 29, 2020.
Combined Search and Examination Report under Sections 17 and 18(3) issued in Great Britain Patent Application No. 1604873.8 dated Sep. 27, 2016.
International Search Report and Written Opinion issued in PCT Patent Application No. PCT/GB2017/050749 dated Nov. 9, 2017.
Leow, et al., "Flow Velocity Mapping Using Contrast Enhanced High-Frame-Rate Plane Wave Ultrasound and Image Tracking: Methods and Initial In Vitro and In Vivo Evaluation," *Ultrasound in Medicine and Biology*, vol. 41, No. 11 (2015).
Feng et al., "Determination of Wave Speed and Wave Separation in the Arteries Using Diameter and Velocity," *Journal of Biomechanics*, vol. 43 (2010).
Zhou et al., "Ultrasound Imaging Velocimetry: Effect of Beam Sweeping on Velocity Estimation," *Ultrasound in Med. & Biol.*, vol. 39, No. 9 (2013).
Extended European Search Report issued in European Application No. 20151464 dated Feb. 25, 2020.
Alastruey et al., "Novel wave intensity analysis of arterial pulse wave propagation accounting for peripheral reflections: Novel Wave Intensity Analyisi," *International Journal for Numerical Methods in Biomedical Engineering*, vol. 30, No. 2 (Oct. 16, 2013).
Curtis et al., "Reduced systolic wave generation and increased peripheral wave reflection inchronic heart failure," *Am J Physiol Heart Circ Physiol* (2007).
Sugawara et al., "Clinical usefulness of wave intensity analysis," *Med Biol. Eng Comput*, 47, pp. 197-206 (2009).
Avolio et al., "Effectsof agin on arterial distensibility in populations with high and low prevalence of hypertension: comparison between urban and rural communities in China," *Circulation*, vol. 71, No. 2, pp. 202-210 (1985).
Laurent et al., "Expert consensus of document on arterial stiffness: methodological issues and clinical applications," *European Heart Journal*, pp. 2588-2605 (2006).
Van Popele et al., "Association Between Arterial Stiffness and Atherosclerosis, The Rotterdam Study," *Stroke*, pp. 454-460 (2001).
Manisty et al., "Wave Reflections Predicts Cardiovascular Events in Hypertensive Individuals Independent of Blood Pressure and Other Cardiovascular Risk Factors," *Journal of the American College of Cardiology*, vol. 56, No. 1 (2010).
Manisty et al., "Differences in the Magnitude of Wave Reflection Account for Differentail Effects of Amlodipine—Versus Atenolol-Based Regimens on Central Blood Pressure: An Anglo-Scandinavian Cardiac Outcome Trial Substudy," *Hypertension Journal of the American Heart Association*, (2009).
Bradlow et al., "Assessing Normal Pulse Wave Velocity in the Proximal Pulmonary Arteries Using Trasnit Time: A Feasibility, Repeatability, and Observer Reproducibility Study by Cardiovascular Magnetic Resonance," *Journal of Magentic Resonance Imaging*, pp. 974-981 (2007).
Taviani et al., "Age-Related Changes of Regional Pulse Wave Velocity in the Descending Aorta Using Fourier Velocity Encoded M-Mode," *Magnetic Resonance in Medicine*, pp. 261-268 (2011).
O'Rourke et al., "Clinical Applications of Arterial Stiffness; Definitions and Reference Values," *American Journal of Hypertension, Ltd.*, pp. 426-444 (2002).
Khir et al., "Determination of wave speed and wave separation in the arteries," *Journal of Biomechanics*, 34, pp. 1145-1155 (2001).
Parker et al., "What stops the flow of blood from the heart?" *Heart and Vessels*, pp. 241-245 (1988).
Barker, Kim H., "An Introduction to Wave Intensity Analysis," http://www.bg.ic.ac.uk/research/k.parker/wave_intensity_web/welcome.html (2018).
Sen et al., "Development and Validation of a New Adenosine-Independent Index of Stenosis Severity From Coronary Wave-Intensity Analysis," *Journal of the American College of Cardiology*, vol. 59, No. 15 (2012).
Beulen et al., "Toward Noninvasive Blood Pressure Assessment in Arteries by Using Ultrasound," *Ultrasound in Med. & Biol.*, vol. 37, pp. 788-797 (2011).
Feng et al., "Determination of wave speed and wave separation in the arteries using diameter and velocity," *Journal of Biomechanics*, pp. 455-462 (2010).
Biglino et al., "Pressure-wave energy relationship during IABP counterpulsation in a mock circulation: changes with angle and assisting frequency," *Int J Artif Organs*, pp. 15-24 (2012).
Tsai et al., "Usefulness of Vascular Wall Deformation for Assessment of Carotid Arterial Stiffness and Association With Previous Stroke in Elderly," *American Journal of Hypertension*, (2013).
Kolyva et al., "A Mock Circulatory System with Physiological Distribution of Terminal Resistance and Compliance: Application for Testing the Intra-Aortic Balloon Pump," *Artificial Organs*, pp. E62-E70 (2012).
Li et al., "Using Magnetic Resonance Imaging Measurements for the Determination of Local Wave Speed and Arrival Time of

(56) References Cited

OTHER PUBLICATIONS

Reflected Waves in Human Ascending Aorta," *32nd Annual International Conference of the IEEE EMBS* (2010).
Poelma et al., "3D Flow reconstruction using ultrasound PIV," *Exp Fluids*, pp. 777-785 (2011).
Poelma et al., "Ultrasound imaging velocimetry: Toward reliable wall shear stress measurements," *European Journal of Mechanics B/Fluids*, pp. 70-75 (2012).
Poelma et al., "Enhancing the dynamic range of ultrasound imaging velocimetry using interleaved imaging," *Meas. Sci. Technol.*, (2013).
Segers et al., "Wave reflection leads to over- and underestimation of local wave speed by the PU- and QA-loop methods: theoretical basis and solution to the problem," *Institute of Physics and Engineering in Medicine* (2014).
Li et al., "Experimental validation of non-invasive and fluid density independent methods for the determination of local wave speed and arrival time of reflected wave," *Journal of Biomechanics*, pp. 1393-1399 (2011).
Lee et al., "Temporal Characterization of the Functional Density of the Vasa Vasorum by Contrast-Enhanced Ultrasonography Maximum Intensity Projection Imaging," *The American College of Cardiology Foundation*, vol. 3, No. 12 (2010).
Arnolda et al., "Adriamycin cardiomyopathy in the rabbit: an animal model of low output cardiac failure with activation of vasoconstricor mechanisms," *Cardiovascular Research*, pp. 378-382 (1985).
Weinberg et al., "Characteristics of the pulse waveform during altered nitric oxide synthesis in the rabbit," *British Journal of Pharmacology*, pp. 361-370 (2001).
Nier et al., "Evidence for a specific influence of the nitrergic pathway on the peripheral pulse waveform in rabbits," *Exp Physiol*, pp. 503-512 (2008).
Morikawa, Y., "Characteristic Pulse Wave casued by Organic Nitrates," *Nature Publishing Group*, (1967).
Takaya et al., "Evaluation of exercise capacity using wave intensity in chronic heart failure with normal ejection fraction," *Heart Vessels*, (2012).
Vriz et al., "One-point carotid wave intensity predicts cardiac mortality in patients with congestive heart failure and reduced ejection fraction," *Int. J. Cardiovascular Imaging*, pp. 1369-1378 (2015).
Li, Y., "Clinical Value of Carotid Wave Intensity Analysis for Differentiating Nonobstructive Hypertrophic Cardiomyopathy from Left Ventricular Hypertrophy Secondary to Systemic Hypertension," *Wiley Periodicals*, vol. 41, No. 3 (2013).
Wang et al., "Tetrahydrobiopterin Improves Endothelial Function in Cardiovascular Disease: A Systematic Review," *Evidence-Based Complementary and Alternative Medicine*, vol. 2014 (2014).
Kovamees et al., "Arginase inhibition improves endothelial function in patients with familial hypercholesterolaemia irrespective of their cholestorel levels," *Journal of Internal Medicine*, (2015).
Celermajer et al., "Non-invasive detection of endothelial dysfunction in children and adults at risk of atherosclerosis," *The Lancet*, vol. 340, No. 8828 (1992).
Xu et al., "Non-invasive endothelial function testing and the risk of adverse outcomes: a systematic review and meta-analysis," *European Heart Journal—Cardiovascular Imaging*, pp. 736-746 (2014).

Al-Qaisi et al., "Measurement of endothelial function and its clinical utility for cardiovascular risk," *Vascular Health and Risk Management*, pp. 647-652 (2008).
Thijssen et al., "Does arterial shear explain the magnitude of flow-mediated dilation?: a comparison between young and older humans," *Am J Physiol Circ Physiol*, (2009).
Yildiz et al., "Correction of Non-Linear Propagation Artifact in Contrast-Enhanced Ultrasound Imaging of Carotid Arteries: Methods and In Vitro Evaluation," *Ultrasound in Med. & Biol.*, vol. 41, No. 7 pp. 1938-1947 (2015).
Cheung et al., "Attenuation Correction and Normalisation for Quantification of Contrast Enhancement in Ultrasound Images of Carotid Arteries," *Ultrasound in Med. & Biol.*, pp. 1-8 (2015).
Davies et al., "Use of simultaneous pressure and velocity measurements to estimate arterial wave speed at a single site in humans," *Am. J. Physiol Heart Circ Physiol*, (2006).
Rabben et al., "An ultrasound-based method for determining pulse wave velocity in superficial arteries," *Journal of Biomechanics*, pp. 1615-1622 (2004).
Wang et al., "Time-domain representation of ventricular-arterial coupling as a windkessel and wave system," *Am J Physiol Heart Circ PHysiol*, (2003).
Stergiopulos et al., "Nonlinear Separation of Forward and Backward Running Wavesin Elastic Conduits," *J. Biomechanics*, vol. 26, No. 2, pp. 201-209 (1993).
Tanter et al., "Ultrafast Imaging in Biomedical Ultrasound," *IEEE Transactions on Ultrasonics, Ferroelectrics, and Frequency Control*, vol. 61, No. 1 (2014).
Mehrad et al., "Ultrasonographic Analysis Versus Histopathologic Evaluation of Carotid Advanced Atherosclerotic Stenosis in an Experimental Rabbit Model," *Ultrasound in Med. & Biol.*, vol. 38, No. 8, pp. 1391-1403 (2012).
Townsend et al., "Recommendations for Improving and Standardizing Vascular Research on Arterial Stiffness," *Vascular Research on Arterial Stiffness*, (2015).
Atkinson et al., "The percentage flow-mediated dilation index: A large-sample investigation of its appropriateness, potential for bias and casual nexus in vascular medicine," *Vascular Medicine* (2013).
Vulliemoz et al., "Estimation of Local Aortic Elastic Properties with MRI," *Magnetic Resonance in Medicine*, pp. 649-654 (2002).
Bohs, L., "A Novel Method for Angle Independent Ultrasonic Imaging of Blood Flow and Tissue Motion," *IEEE Transactions on Biomedical Engineering*, vol. 38, No. 3 (Mar. 1991).
Bohs, L., "Ensemble Tracking for 2D Vector Velocity Measurement: Experimental and Initial Clinical Results," *IEEE Transactions on Ultrasonics, Ferroelectrics, and Frequency Control*, vol. 45, No. 4 (Jul. 1998).
Khir et al., "Determination of wave intensity in flexible tubes using measured diameter and velocity," *Proceedings of the 29th Annual International Conference of the IEEE EMBS* (Aug. 2007).
Trahey et al., "Adaptive Clutter Filtering via Blind Source Separation for Two-Dimensional Ultrasonic Blood Velocity Measurement," *Ultrasonic Imaging*, 24, pp. 193-214 (2002).
Nielsen et al., "In-vivo Examples of Flow Patterns With the Fast Vector Velocity Ultrasound Method," *Ultraschall in Med*, pp. 471-477 (2009).
Office Action issued in Chinese Patent Application No. 201780029789.5 dated Feb. 26, 2021.

\* cited by examiner

FLUID FLOW ANALYSIS

TECHNOLOGICAL FIELD

The present invention relates to methods and apparatus for using ultrasound to analyse fluid flow in fluid conduits. In particular, though not exclusively, the invention applies to such methods and apparatus useful for analysing fluid flows in human or animal circulatory systems.

BACKGROUND

When the heart contracts during each heartbeat, it increases the pressure and speed of the blood in the arteries immediately connected to it. This disturbance propagates as a wave down the arterial system. An everyday example of this phenomenon is that the pulse can be felt in the wrist. The wave travels at a speed or velocity that depends on the stiffness of the arteries, and reflections of the wave occur at any point where the vessel geometry or wall properties change. The velocity of the waves and the intensity of the initial wave and its reflections therefore contain information about the performance of the heart and the state of the vessels. It is therefore useful to measure these properties to provide a useful means for diagnosing cardiovascular disease and those at risk from it.

Pulse waves in arteries can therefore be used for assessing (a) the performance of the heart, since it generates the waves, (b) arterial stiffness, which determines the velocity of the waves, and (c) changes in arterial or peripheral vessel cross section or mechanical properties, which reflect the waves. Wave phenomena can readily be assessed from invasive, catheter-based measurements and are increasingly used for the functional assessment of coronary artery stenosis. Their use in other areas of cardiovascular medicine has been impeded by the difficulty of making accurate, non-invasive measurements.

SUMMARY OF THE DISCLOSURE

It is an object of the invention to provide a method and apparatus for analysis of fluid flows in fluid conduits such as arteries which can preferably be implemented non-invasively. In one aspect, the invention seeks to provide an ultrasound-based system for assessing wave phenomena that is non-invasive and suitable for the clinical investigation of heart failure, arterial stiffening, altered vascular tone and endothelial dysfunction, for example.

According to one aspect, the invention provides a method of determining a measure of wave speed in a fluid flowing through a fluid conduit, the method comprising:
using ultrasound measurements to determine the conduit diameter or conduit cross-sectional area, as a function of time, at a longitudinal position of the conduit;
using ultrasound measurements to determine fluid velocity, as a function of time, in a volume element at said longitudinal position of the conduit, the ultrasound measurement to determine fluid velocity being effected by tracking objects within the fluid flow in successive frames sampling the volume element, and obtaining displacement vectors for the objects;
determining a wave speed from a function of (i) the change in fluid velocity at the longitudinal position as a function of time and (ii) the change in the conduit diameter as a function of time.

The wave speed may be determined from a ratio of the change in fluid velocity at the longitudinal position as a function of time and the change in a logarithmic function of the conduit diameter as a function of time. The wave speed may be determined from a ratio of a change in fluid velocity at the longitudinal position within a time interval and a corresponding change in a logarithmic function of the conduit diameter within the same time interval. The wave speed may be determined from the change in fluid velocity at the longitudinal position within a time interval and a corresponding change in the conduit diameter within the same time interval. The fluid velocity may be determined using imaging velocimetry. The ultrasound measurements for determining fluid velocity may comprise a series of B-mode images or B-mode RF data. Obtaining displacement vectors may comprise correlating the locations of the tracked objects in successive frames of the B-mode images or B-mode RF data. The ultrasound measurements for determining conduit diameter and fluid velocity may be both derived from a common ultrasound transducer head. The common transducer head may be directed orthogonally to the fluid flow axis of the fluid flow conduit. The ultrasound measurements for determining conduit diameter and fluid velocity may be both derived from common ultrasound excitation and response signals. The ultrasound measurements for determining conduit cross-sectional area and fluid velocity may be both derived from common ultrasound excitation and response signals. The wave speed, c, may be determined according to the equation $c = 0.5(dU/d\ln D)$, where $dU$ is a change in the fluid velocity as a function of time and $d\ln U$ is a change in the natural logarithm of $D$ as a function of time. The fluid conduit may comprise a part of the human or animal circulatory system. The method may include repeating the ultrasound measurements and determining a wave speed at multiple times during a cardiac cycle and correlating the measurement of wave speed with time within the cardiac cycle. The method objects being tracked may comprise red blood cells, white blood cells, platelets or contrast agent entities. The method may include determining a measure of fluid conduit wall elasticity or distensibility at the volume element, from the wave speed. The wave speed, c, may be determined according to the equation $c = AdU/dA$ or $c = dU/d\ln A$, where $A$ is the cross-sectional area, $dA$ is the change in cross-sectional area as a function of time, $dU$ is the change in the fluid velocity, and $d\ln A$ is the change in the natural logarithm of $A$ as a function of time.

According to another aspect, the invention provides a method of determining a measure of wave speed in a fluid flowing through a fluid conduit, the method comprising:
using ultrasound measurements to determine the conduit diameter, as a function of time, at a longitudinal position of the conduit;
using ultrasound measurements to determine fluid velocity, as a function of time, in a volume element at said longitudinal position of the conduit, the ultrasound measurement to determine fluid velocity being effected by tracking objects within the fluid flow in successive frames sampling the volume element, and obtaining displacement vectors for the objects;
determining a change in flow rate through the conduit based on the fluid velocity measurements and the conduit diameter measurements;
determining a change in cross-sectional area of the conduit based on the conduit diameter measurements; and
determining a wave speed from a ratio of the change in flow rate at the longitudinal position as a function of time and the change in conduit cross-sectional area as a function of time.

The fluid velocity may be determined using imaging velocimetry. The ultrasound measurements for determining fluid velocity may comprise a series of B-mode images or B-mode RF data. Obtaining displacement vectors may comprise correlating the locations of the tracked objects in successive frames of the B-mode images or B-mode RF data. The ultrasound measurements for determining conduit diameter and fluid velocity may be both derived from a common ultrasound transducer head. The common transducer head may be directed orthogonally to the fluid flow axis of the fluid flow conduit. The ultrasound measurements for determining conduit diameter and fluid velocity may be both derived from common ultrasound excitation and response signals. The wave speed, c, is determined according to the equation c=dQ/dA), where dQ is a change in the fluid flow rate and dA is a change in the cross-sectional area of the conduit. The fluid conduit may comprise a part of the human or animal circulatory system. The method may include repeating the ultrasound measurements and determining a wave speed at multiple times during a cardiac cycle and correlating the measurement of wave speed with time within the cardiac cycle. The objects being tracked may comprise red blood cells, white blood cells, platelets or contrast agent entities. The method may include determining a measure of fluid conduit wall elasticity or distensibility at the volume element, from the wave speed.

A method of determining a measure of wave intensity in a fluid conduit, the method comprising:

using ultrasound measurements to determine the conduit diameter, as a function of time, at a longitudinal position of the conduit;

using ultrasound measurements to determine fluid velocity, as a function of time, in a volume element at said longitudinal position of the conduit, the ultrasound measurement to determine fluid velocity being effected by tracking objects within the fluid flow in successive frames sampling the volume element, to obtain displacement vectors for the objects;

determining a measure of wave intensity as a function of change in determined conduit diameter and corresponding change in fluid velocity.

The fluid velocity may be determined using imaging velocimetry. The ultrasound measurements for determining fluid velocity may comprise a series of B-mode images or B-mode RF data, and obtaining displacement vectors comprises correlating the locations of the tracked objects in successive frames of the B-mode images or B-mode RF data. The ultrasound measurements for determining conduit diameter and fluid velocity may be both derived from a common ultrasound transducer head. The common transducer head may be directed orthogonally to the fluid flow axis of the fluid flow conduit. The ultrasound measurements for determining conduit diameter and fluid velocity may be both derived from common ultrasound excitation and response signals. The method may include determining a wave speed in the fluid conduit. The measure of wave intensity may be determined as a function of the determined conduit diameter, the determined fluid velocity and the determined wave speed. The measure of wave intensity may be determined according to the equation:

$$dI_\pm = \frac{1}{4(D/2c)}\left(dD \pm \frac{D}{2c}dU\right)^2$$

where $dI+$ is the forward wave intensity, $dI-$ is the backward wave intensity; D is the conduit diameter; dD is the change in the conduit diameter; c is the wave speed; dU is the change in fluid velocity. The measure of wave intensity is determined according to the equation dI=dDdU, where dI is the wave intensity; dD is the change of conduit diameter; and dU is the change of fluid velocity. The method may include determining wave energy by integrating the wave intensity over a period of time. The wave speed may be determined as a function of a ratio of the change in fluid velocity at the longitudinal position as a function of time and the change in a logarithmic function of the conduit diameter as a function of time. The wave speed, c, may be determined according to the equation c=0.5(dU/dlnD), where dU is a change in the fluid velocity as a function of time and dlnU is a change of the natural logarithm of D as a function of time. The fluid conduit may comprise a part of the human or animal circulatory system. The method may include repeating the ultrasound measurements and determining a wave intensity at multiple times during a cardiac cycle and correlating the measurement of wave intensity with time within the cardiac cycle. The objects being tracked may comprise red blood cells, white blood cells, platelets or contrast agent entities. The method may include determining a measure of fluid conduit cross-sectional properties upstream and or downstream of the sampled volume element from the wave intensity. The method may include determining a cardiac output profile from the wave intensity.

According to another aspect, the invention provides an apparatus for determining a measure of wave speed in a fluid conduit, comprising an analysis module configured to perform the steps of any of the methods of determining wave speed as described above.

According to another aspect, the invention provides an apparatus for determining a measure of wave intensity in a fluid conduit, comprising an analysis module configured to perform the steps of any of the methods of determining wave intensity as described above.

BRIEF DESCRIPTION OF THE FIGURES

Embodiments of the present invention will now be described by way of example and with reference to the accompanying drawings in which.

DETAILED DESCRIPTION

Figure 1:
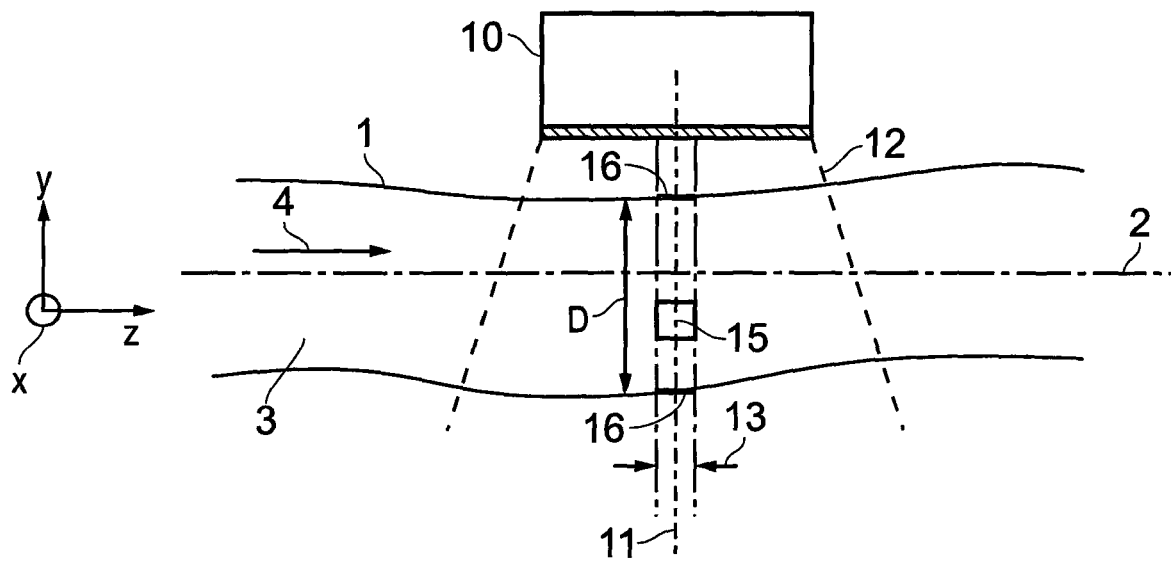
FIG. 1 is a schematic diagram of a fluid conduit and ultrasound transducer in cross-section useful in explaining a fluid flow analysis technique.

Arterial Pulse Waves and their Relation to Clinically Important Cardiovascular Properties a) Wave Fundamentals Pulse waves originate from the heart and travel forwards from the proximal (upstream) end of the arterial system towards the periphery. Reflections originate more peripherally, at sites where vascular properties change; the reflected waves travel backwards, and can then re-reflect forwards and backwards between reflection sites until they dissipate. Pushing more blood into the artery gives a compression wave whereas suction gives a decompression wave. A compression wave will increase pressure and accelerate flow if it originates proximal to the measurement site, whilst a decompression wave will decrease pressure and retard flow. Methods described in this disclosure may generally relate to measuring the speed and/or intensity and/or reflection of such compression/decompression waves travelling through a fluid flowing in a fluid conduit such as the circulatory system. The waves may generally be considered to comprise disturbances in fluid pressure, fluid velocity and fluid conduit diameter that propagate along the fluid conduit with time. In preferred arrangements exemplified herein, the fluid is blood and the fluid conduits comprise blood vessels and components of the circulatory system.

b) Waves and Cardiac Performance

The left ventricle generates forward-going waves in non-coronary systemic arteries. A compression wave arises at the start of systole because the contraction of the ventricle causes the pressure and flow of blood to increase. A forward expansion wave that arises in late systole is thought to be generated by momentum, which carries the blood forward as ventricular contraction slows and then relaxes, resulting in a decrease in pressure and flow. These waves are altered in clinically-important conditions. For example, the left ventricle produces a smaller compression wave in patients with systolic heart failure, including dilated cardiomyopathy [1, 2], whereas hypertrophic cardiomyopathy causes diastolic dysfunction and results in a less powerful expansion wave [2].

c) Local Arterial Compliance

The speed, c, of wave travel in arteries is conventionally termed Pulse Wave Velocity (PWV). It is related to the distensibility of the wall and the density of blood by the Bramwell Hill equation $$c^2 = 1/(\text{density} \times \text{distensibility}).$$

Hence PWV is a measure of arterial stiffness: the stiffer the artery, the faster the wave speed. Peripheral arteries have a higher PWV than central ones, and arteries stiffen with age [3]. PWV is clinically important because it is a strong, independent cardiovascular risk factor [4], and because arteries stiffen when they become diseased [5].

Elasticity of a blood vessel can be obtained from wave speed (or PWV) by the Moens-Korteweg equation:

$$c^2 = (E_{inc} h)/(2r\ rho)$$

where $E_{inc}$ is the incremental elastic modulus, h is the vessel wall thickness, r is the vessel radius, and rho ($\rho$) is blood density.

A stretchy artery has low elastic modulus and high distensibility, so for the same vessel (i.e. for the same h and r), they are reciprocally related:

$$\text{Distensibility} = (2r)/(h\ E_{inc}).$$

d) Wave Reflections

Pulse waves are reflected at vascular sites where there is a change in cross-sectional area or wave speed. Changes in area occur at sites of branching or taper, and changes in wave speed occur where wall structure alters. Wave reflections are clinically important; the ASCOT trial, for example, showed increased reflection to be a strong independent predictor of cardiovascular events in hypertensives [6]. Wave reflections can account for the different left ventricular masses in patients taking different anti-hypertensive medication, despite similar brachial blood pressures [7], and they maintain systolic blood pressure in patients with heart failure [1].

Measurement of Arterial Pulse Wave Characteristics

PWV has been assessed by transit time methods. In an invasive transit-time technique, a catheter having two pressure sensors a known distance apart is inserted into an artery, and the time delay between the arrival of the pressure wave at the two sites is used in conjunction with their separation to find the wave speed. Non-invasive assessment of PWV using this principle is also possible. Detection can be based on pressure measured by applanation tonometry, velocity measured using Doppler ultrasound, or volume measured by photoplethysmography. It is also possible to make measurements with MRI [9,10] but this may be too costly for routine use. Sites are much further apart than with the invasive technique: typically, transit times between the carotid and femoral arteries are assessed.

The catheter-based method is considered too invasive for routine use in people. Unfortunately, the non-invasive methods also suffer from limitations. First, it is difficult to obtain an accurate value for the path-length from the heart to each of the measuring sites, especially in patients with obesity or tortuous vessels. Second, the methods give a PWV averaged over several vessels, rather than local values. That is an important issue because different arteries stiffen with age at different rates [3] and have different relations to disease [10,11]; local measurements should have much greater clinical value (although since they are less widely used, there have been few attempts to validate their predictive value). Third, femoral waveforms may be difficult to record accurately or may be modified in patients with a range of medical conditions. Fourth, and most importantly, all these methods assess the velocity of the waves but not their intensity or reflection.

Attempts have been made to overcome these issues by developing methods for obtaining PWV at a single site. That eliminates the problems associated with averaging PWV over large arterial distances and obviates the need for estimating those distances. Additionally, the measurements required for determining PWV at a single site generally also make it possible to analyse wave intensities and reflections, as explained below. Theoretically, then, such techniques could be of great value.

In these single-site methods, wave properties are determined by continuously and simultaneously measuring both blood pressure (P) and blood velocity (U). PWV can be derived from the ratio of the change in P (dP) to the change in U (dU) between successive measurements, if P and U are measured during phases of the cardiac cycle when forward waves dominate [12]. Further characterisation of the waves was revolutionised by the Wave Intensity Analysis (WIA) methods developed over the last 20 years by Parker and co-workers [13]; an on-line tutorial is given at [14]. Their mathematical derivation is complex but the equations derived for their practical application are straightforward. The wave intensity, dI, at any time in the cardiac cycle is obtained from the product of dP and dU. Knowing PWV (see above) additionally allows the wave to be decomposed into forward and backward components.

P and U can be measured invasively with catheter-based arterial probes. This method has been used in many WIA studies, for example where WIA is used to determine the severity of coronary stenosis [15]. However, the invasive nature of the technique is highly restrictive. Attempts have therefore been made to develop non-invasive alternatives.

In locations where arteries overlie hard structures and are relatively close to the body surface, P can be measured by applanation tonometry and U by Doppler ultrasound [1]. Utility is limited by the number of vessels that can be accessed in this way, as well as by the need to calibrate the tonometer data. (Peak systolic pressures vary between arteries due to different patterns of wave reflection; hence, pressures should be assessed by sphygmomanometry of the brachial artery to obtain absolute mean and diastolic pressures —these are constant throughout the arterial system and can therefore be used to calibrate tonometric measurements from the vessel of interest. Alternatively, pressures could be assessed by tonometry that has been calibrated by sphygmomanometry of the same vessel.) Most importantly, it is impossible to apply both probes to the same site at the same time; this means that the P and U data streams have to be acquired separately, ensemble averaged and then time aligned by the ECG, introducing significant errors.

Another non-invasive method [2] has been implemented which uses a combination of Doppler and M-Mode ultrasound to measure U and arterial diameter D, respectively. A linear relation between the diameter of the artery and the pressure inside it is assumed, in order to obtain the P required for conventional WIA. The use of Doppler and M-Mode can be problematic since these modes require different beam angles, making it difficult to image the same arterial segment. Furthermore, the calibration of the pressure-diameter relationship is complex, as just described for tonometry. (In practice this is so involved that it is rarely done, and carotid diameters are incorrectly calibrated by simple brachial sphygmomanometry.) Finally, the assumption that P and D are proportional is fundamentally incorrect since arteries have non-linear stress-strain curves. Beulen et al [16] have suggested methods to overcome this last issue by non-linearly estimating P from D, but these involve a long chain of assumptions and have not been tested under physiological conditions. Another technique combining Doppler with B-mode or M-mode ultrasound is given in [55].

The invention overcomes the limitations of existing systems because it obviates the need for measuring P (invasively) or estimating it (inaccurately) from measurements of diameter, D.

An alternative form of WIA is based directly on U and D, rather than U and P [17]. PWV can be obtained from the ratio of the change in U to the simultaneous change in the natural logarithm of D (preferably, at a point in the cycle when forward waves dominate):

$$c = 0.5(dU/d\ln D).$$

Wave intensity is given by:

$$dI_\pm = \frac{1}{4(D/2c)}\left(dD \pm \frac{D}{2c}dU\right)^2$$

where dI+ is the forward wave intensity, dI− is the backward wave intensity; D is the conduit diameter; dD is the change of the conduit diameter; c is the wave velocity; dU is the change of fluid velocity.

This analysis technique has been validated in silicon model systems [18] (including a geometrically and mechanically accurate model of the human aorta and its major branches [19]) and with data acquired in human aortas by Dr Wilkinson and colleagues (Cambridge), using MRI [20].

Ultrasound may be used to obtain the D and U data required by this new analysis technique, thereby avoiding the use of costly MRI. Conventional ultrasound B-mode methods can be used to determine D. To avoid the problem of different beam angle requirements inherent in Doppler and M-mode measurements (discussed above), in a new technique described herein, Doppler ultrasound is not used to determine U. Instead, a form of particle image velocimetry known as ultrasound image velocimetry (UIV) is used. In this method, a series of B-mode images, or the radio-frequency (RF) data from which they derive, is acquired and regional cross correlation is performed on sequential images to determine the local displacement of the ultrasound scatterers. The ultrasound scatterers may be any suitable objects, such as red blood cells, white blood cells, platelets or microbubble contrast agents, which can be tracked through consecutive image frames. From these displacements, and the acquisition frame rate, a full 2-D velocity field is found. Combining the axial velocities obtained by this method with the new WIA equations means that for the first time, wave velocities, intensities and reflections can be obtained non-invasively, without unreliable conversion of D to P, from data streams obtained simultaneously at the same location.

With reference to FIG. 1, a fluid conduit 1 has a longitudinal axis 2 which may be referred to as the z-axis and conveys a fluid 3 therethrough with a dominant flow direction 4 generally along the z-axis. In an example, the fluid conduit 1 may be a vessel in the human or animal circulatory system. An ultrasound transducer 10 is positioned to direct ultrasonic excitation energy along a beam axis 11 which is transverse to the fluid conduit longitudinal axis 2, and preferably is orthogonal to the fluid conduit longitudinal axis 2, i.e. the beam axis 11 is on the y-axis as shown, the x-axis being into the plane of the drawing. The transducer preferably comprises an array of transducer elements.

The ultrasound transducer 10 generates an excitation beam 12 comprising excitation signals configured to sample a longitudinal position or extent 13 of the conduit 1 along the z-axis and a lateral extent along the x-axis. The transducer 10 receives response signals, from which are generated a succession of image frames. At least a part of each image frame represents a volume element 15. The volume element 15 represents a finite segment of the conduit along the z-axis, and may represent a portion of the conduit in x- and y-space (orthogonal to the dominant flow axis) or may represent a full slice through the conduit, i.e. the full conduit width in one or both of x and y. In a basic configuration, UIV is performed on the volume element which is a full slice through the conduit diameter and the stated finite segment of the conduit along the z-axis, and variation in wave velocity across the conduit diameter is not considered.

Each image frame provides a spatial map of ultrasound-scattering objects in the flow and correlation of successive image frames enables the velocity of selected objects passing through the volume element 15 to be determined, in accordance with established ultrasound imaging velocimetry techniques. The objects may, for example, be red blood cells, white blood cells or platelets in blood flow through an artery in the human or animal circulatory system. The objects may, for example, be microbubble contrast agents within the blood flow. More generally, the objects may be any objects such as single particles or clumps of particles capable of being distinguished in the ultrasound images from received ultrasound echo signals. In one arrangement, identifiable objects in the first image of the volume element 15 are identified in a successive, e.g. second, image of the volume element to see how far the objects have travelled. The objects may be speckles or speckle patterns. The identification of the objects in the second image may be performed using an autocorrelation method. The autocorrelation method may be applied to groups of objects.

The ultrasound transducer 10 may also be configured to transmit ultrasound excitation signals to the conduit 1 and to receive corresponding ultrasound response signals indicative of the positions 16 of the conduit walls. Successive measurements are used to determine changes in diameter D of the conduit 1 at the longitudinal position 13, which measurements are correlated in time with corresponding object velocity measurements. The transducer 10 effecting the velocity measurements and the transducer effecting the conduit wall positions 16 may comprise the same transducer head.

The fluid flowing in the conduit 1 is subject to pressure waves such as those caused by the heart pumping action, arterial elasticity and arterial topology as discussed earlier. The wave velocity of such pressure waves may be determined according to the expression $c=0.5(dU/d\ln D)$, where dU is a change in the fluid velocity as a function of time and $d\ln D$ is a change in the natural logarithm of D as a function of time. The expression "as a function of time" is intended to encompass any changes determined by successive measurements of the relevant property at known time intervals such as unit time intervals (e.g. the ultrasound imaging frame rate) or variable time intervals, or at times when two different properties being measured can be correlated to a common point in time or time interval, as well as an instantaneous measurement of the first time derivative of that property. In a preferred arrangement, D and U are determined periodically according to the frame rate of the ultrasound transducer 10. In another arrangement, $dU/dt$ and $d\ln D/dt$ may be used to determine wave speed or velocity.

The change in fluid velocity within the volume element 15 may be determined by measuring the fluid velocity at two or more successive times, e.g. using the ultrasound imaging velocimetry technique. The change in the logarithmic function of D may be determined by measuring the diameter from the ultrasound response signals at the same two or more successive times.

Wave velocity c can then be determined by direct computation of the ratio of these two changes. Alternatively, the rate of change of fluid velocity, $dU/dt$, may be determined for a sample period and the rate of change of the logarithmic function of conduit diameter, $d\ln D/dt$, may be determined for a corresponding, but not necessarily identical, sample period. The sample periods are preferably coextensive or overlapping or contiguous, but in any event are sufficiently close in time that measured changes in fluid velocity are correlated in time with measured changes in conduit diameter.

In general aspect, the measured fluid velocity U may be that of a single object or group of objects as discussed above, or may be aggregated over a plurality of objects within the volume element. In this respect, the fluid velocity may be expressed as an average fluid velocity for the volume element 15. As stated earlier, the volume element can comprise a full cross-section of the conduit diameter and the average fluid velocity can therefore be the mean velocity across the conduit diameter.

The ultrasound response signals used to derive both fluid velocity and conduit diameter may comprise B-mode image data. The B-mode image data may comprise RF data from which B-mode images may be derived, and the fluid velocity may be determined directly from the RF data. The B-mode image data may comprise B-mode images. The ultrasound response signals used to derive both fluid velocity and conduit diameter may be obtained as responses to common ultrasound excitation signals. The ultrasound response signals used to derive both fluid velocity and conduit diameter may comprise B-mode data. The conduit diameter may be obtained with fewer transducer elements than required for a B-mode image, even down to a single transducer element used more frequently, e.g. M-mode. This could be interleaved with the full B-mode imaging used to obtain the velocity. Use of the M-mode could give a more accurate measure of the diameter as a function of time.

For measurements made in a human or animal circulatory system, the fluid velocity and conduit diameters may be determined at multiple times during each cardiac cycle. The determination of wave velocity may then be determined at multiple times during each cardiac cycle and/or the wave velocity may be determined only at selected times during each cardiac cycle. The wave velocity may be determined at a point in the cardiac cycle when forward waves dominate at the longitudinal position 13.

From the measurements of wave velocity, a measure of the fluid conduit wall elasticity, at the longitudinal position 13 of the volume element 15, may be made.

In an alternative arrangement, the wave velocity may be computed according to a slightly different methodology. The ultrasound data used to determine the conduit diameter D, as a function of time, at the longitudinal position 13 of the conduit 1 may be used to calculate a cross-sectional area A of the conduit as a function of time. The ultrasound measurements used to determine fluid velocity as a function of time, in the volume element 15 at the longitudinal position 13 of the conduit 1, may be used to calculate a total flow rate Q through the conduit as a function of time. Again, the expression "as a function of time" is intended to encompass any changes determined by successive measurements of the relevant property (e.g. Q or A) at known time intervals such as unit time intervals or variable time intervals, or at times when two different properties being measured can be correlated to a common point in time or time interval, as well as an instantaneous measurement of the first time derivative of that property. In a preferred arrangement, Q and A are determined periodically according to the frame rate of the ultrasound transducer 10. The measurements Q and A can be determined from velocity measurements U and diameter measurements D by assuming radial symmetry. Alternatively, with some more recent 3D ultrasound systems, it may be possible to obtain Q and A directly.

The wave velocity c may then be determined according to a ratio of a change in flow rate and a corresponding change in cross-sectional area of the conduit, e.g. $c=dQ/dA$. Change in flow rate through the conduit may be based on successive fluid velocity measurements and conduit diameter measurements. Change in cross-sectional area of the conduit may be based on successive conduit diameter measurements.

The wave velocity c can also therefore be determined according to a ratio of a change in fluid velocity and a corresponding change in cross-sectional area of the conduit, e.g. using a relationship as outlined in [52], $$c=AdU/dA=dU/d\ln A,$$

where A is the cross-sectional area, dA is the change in cross-sectional area, and dU is the change in flow velocity. It can be understood that if changes in area are negligible compared to changes in velocity, then the $c=dQ/dA$ expression [53] would be equivalent to $c=AdU/dA$. Otherwise they are only approximately the same.

Since A, and changes in A, can be determined according to the ultrasound measurements of D, this can be seen as a function of changes in conduit diameter. Thus, in a general aspect, wave speed can be determined from a function of (i) the change in fluid velocity at the longitudinal position as a function of time and (ii) the change in the conduit diameter as a function of time, or wave speed can be determined from a ratio of the change in flow rate at the longitudinal position as a function of time and the change in conduit cross-sectional area as a function of time. It will be understood that in this context, a measure of the change in cross-sectional area in a conduit having a circular cross-section can readily be obtained from the measure of change in cross-sectional diameter. It will also be understood that for a conduit with, e.g. a non-circular cross-section, multiple measurements of diameter (at different angles about the conduit longitudinal axis) or multiple chord measurements (which may or may not include a "diameter" in the strict mathematical sense of a line passing through the centre of the conduit) may be used to determine cross-sectional area and thereby to determine changes in cross-sectional area.

A measure of wave intensity can also be calculated from the ultrasound measurements as described above, and in particular from the determined conduit diameter and fluid velocity. A measure of wave intensity may be determined according to the equation:

$$dI_{\pm} = \frac{1}{4(D/2c)}\left(dD \pm \frac{D}{2c}dU\right)^2$$

where dI+ is the forward wave intensity, dI− is the backward wave intensity; D is the conduit diameter; dD is the change in the conduit diameter; c is the wave speed; dU is the corresponding change in fluid velocity.

A measure of wave intensity can also be determined according to the equation dI=dDdU, where dI is the wave intensity; dD is the change of conduit diameter; and dU is the corresponding change of fluid velocity.

A measure of wave energy, I, can also be determined by integrating the wave intensity dI over a period of time. The period of time may be from the start of a wave to the end of a wave and/or over a predetermined portion of a cardiac cycle. Determining wave energy I may be useful for long lasting waves of low intensity.

From the measure of wave intensity at longitudinal position 13, it is possible to determine a measure of performance of the heart. It is also possible to determine a measure of fluid conduit wall stiffness and cross-sectional properties at the longitudinal position and also both upstream and downstream of the longitudinal position 13 by suitable analysis over the cardiac cycle, for example by analysis of reflections, particularly by calculating the intensity of reflected waves, the reflection coefficients and the distance to reflection sites. The cross-sectional properties may include properties such as wall stiffness, wall thickness, vessel cross-sectional area, branching, bifurcation, pathological alteration of wall properties, etc.

Figure 2:
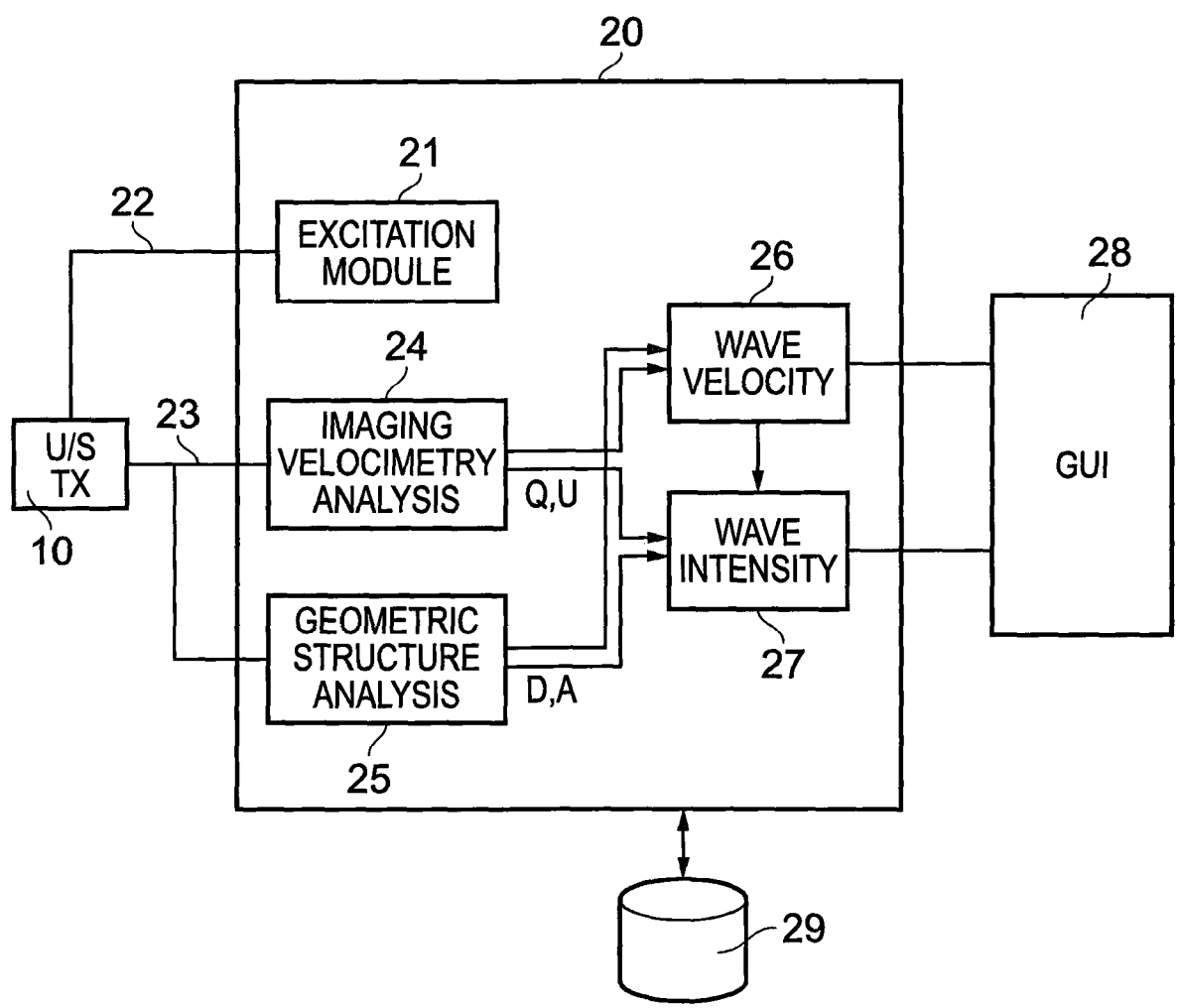
FIG. 2 is a schematic functional block diagram of an ultrasound fluid flow analysis system.

With reference to FIG. 2, an exemplary apparatus for determining wave velocity and wave intensity and wave energy is described.

Ultrasound transducer 10 is coupled to an ultrasound system module 20. An excitation module 21 or driver provides signals 22 to the transducer 10 to generate ultrasound excitation signals for insonification of the fluid conduit 1, particularly adapted to generate response signals from a selected volume element 15 at a longitudinal position 13 of the fluid conduit 1 as seen in FIG. 1. Response signals 23 from the transducer 10 are passed to an ultrasound imaging velocimetry (UIV) analysis module 24 and to a geometric structure analysis module 25. The UIV analysis module 24 is configured to determine a succession of fluid velocity measurements, i.e. to determine fluid velocity as a function of time, using UIV techniques as described above. The UIV analysis module 24 may also or instead be configured to calculate the total flow rate Q through the conduit as a function of time, also as discussed above. The geometric structure analysis module 25 is configured to determine a succession of conduit diameter measurements, i.e. to determine conduit diameter as a function of time, derived from ultrasound response signals from the conduit walls, using techniques as described above. The geometric structure analysis module 25 may also be configured to determine a succession of cross-sectional area measurements of the conduit from the successive diameter measurements.

The measurements of fluid velocity as a function of time and conduit diameter as a function of time are passed to wave velocity analysis module 26 and/or wave intensity analysis module 27.

Wave velocity analysis module 26 is configured to determine wave velocity either (i) from a ratio of the change in fluid velocity and the corresponding change in logarithmic function of conduit diameter, or (ii) from a ratio of the change in flow rate and the change in conduit cross-sectional area, at the longitudinal position 13 of the conduit, using techniques as described above.

Wave intensity analysis module 27 is configured to determine wave intensity as a function of change in conduit diameter and corresponding change in fluid velocity, using techniques as described above.

EXAMPLES

Figure 3A:
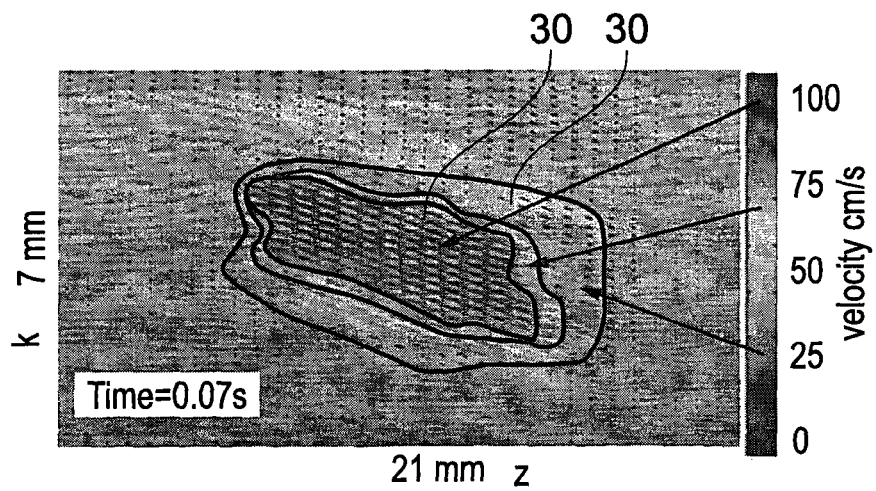
FIGS. 3A-3C show results of fluid velocity measurements in an artery (FIGS. 3A and 3B) and conduit diameter measurement (FIG. 3C)
Figure 3B:
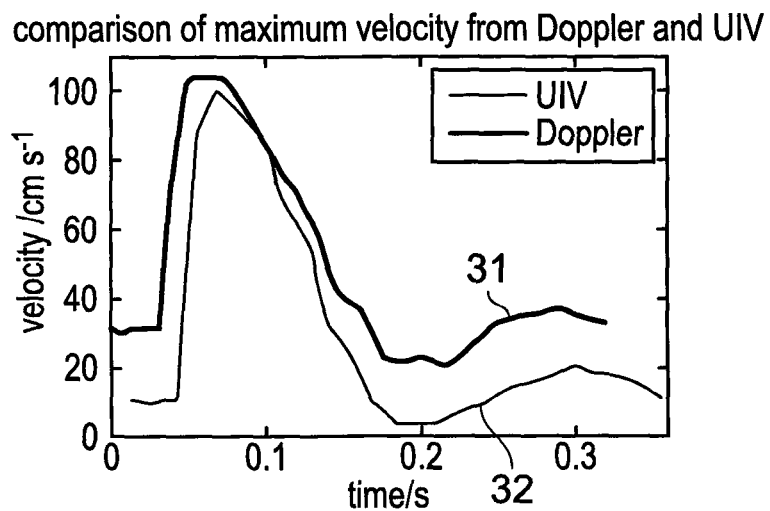
Figure 3C:
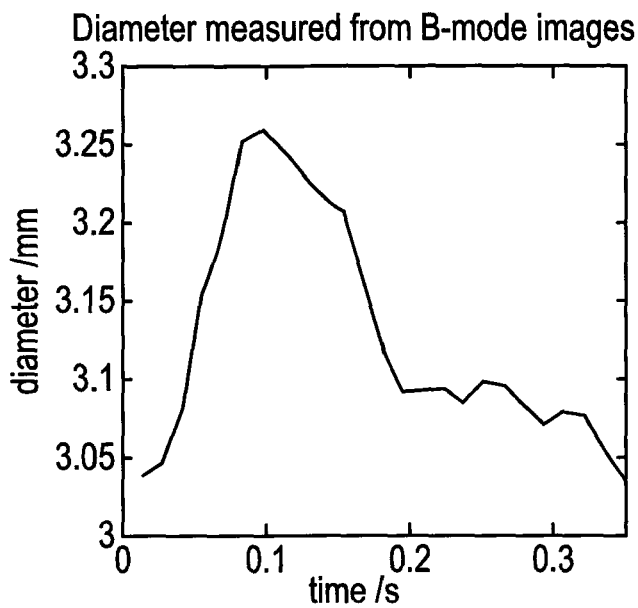

In a preferred arrangement, improved UIV methods such as those described in [21-24] may be used. These were implemented on an Ultrasonix scanner and showed that, although the data were noisy, they give blood flow velocities comparable to theoretical predictions and to invasive measurements in vitro, and that they non-invasively give velocity measurements comparable to those obtained by Doppler ultrasound in a rabbit aorta in vivo as shown in FIGS. 3A-3C. FIG. 3A shows flow velocity data from UIV analysis in the rabbit aorta. Velocity measurements are indicated by the magnitudes of arrows 30 for a plurality of spatial locations along the conduit flow axis (z) and transverse to the conduit flow axis (x). These represent a velocity vector field overlaid on an ultrasound B-mode image. Any one or more of these velocity measurements 30 may be used to derive the velocity in a volume element 15 of FIG. 1. A succession of such velocity measurements 30 over time, which may be averaged over the conduit cross-section, may be used to derive fluid velocity as a function of time, as discussed above, and thereby change in velocity. A set of the velocity measurements 30 through a cross-section of the fluid conduit (e.g. all measurements 30 along a cross-sectional (x) axis may be used to determine a flow rate through the conduit. FIG. 3B shows maximum measured velocity from a Doppler spectrum (line 31) from a Doppler ultrasound technique compared to maximum velocity as measured by the UIV technique (line 32). FIG. 3C shows a measurement of conduit diameter (aorta diameter) measured from the B-mode images using a simple intensity peak method.

From the UIV data, diameters obtained from the same scans, and the new approach described herein, we calculated a wave speed of 3.6 m/s, which is well within the accepted range of values.

Ultrafast ultrasound imaging systems have recently been developed for medical applications [25]. They beam-form and acquire data from all transducer elements in parallel instead of line by line, giving a frame rate up to two orders of magnitude higher than conventional scanners. The technique is likely to form the basis of the next generation of clinical scanners. For our purposes, the massively increased frame rate enables more accurate tracking of the rapid changes in flow and diameter that occur in arteries, and it also reduces signal-to-noise ratios by allowing averaging of repeat measurements even while meeting the stringent temporal resolution requirements. We have implemented UIV on the new system and validated it in straight tubes, arterial phantoms and in the rabbit aorta by comparison against analytical solutions and Doppler measurements [26]; data quality was vastly improved by the higher frame rate [26].

The ultrasound system module 20 of FIG. 2 may be further adapted to include a real-time graphical user interface 28 that shows a current B-mode image and a preliminary estimate of velocity from UIV, allowing a user to select a region for analysis.

The system module 20 may further include a semi-automated echo tracking method for monitoring arterial diameter. The position of the luminal surface of upper and lower conduit walls may first be marked manually, e.g. using interface 28. A cross correlation of the RF signals may then be used to track their position and hence obtain changes in conduit diameter D.

Imaging and UIV variables such as plane wave steering angles and UIV tracking window sizes may be optimised for accuracy and precision. RF data filtering may be incorporated to optimise the ultrasound signals for UIV measurements.

A recently-described factor [27] that corrects PWV for effects of wave reflections may be incorporated into the control software of the system module 20.

All data from the system may be transmitted to a database 29 for further processing. Wave velocity and/or wave intensity analysis modules 26, 27 may be provided as separate apparatus, e.g. for off-line processing and calculation of wave speed, intensity and reflection from data captured to the database 29.

The system 20 may be used to detect circulatory abnormalities in humans and animals by monitoring changes in wave intensities, which are altered in heart failure patients, using the non-invasive techniques described.

Figure 4A:
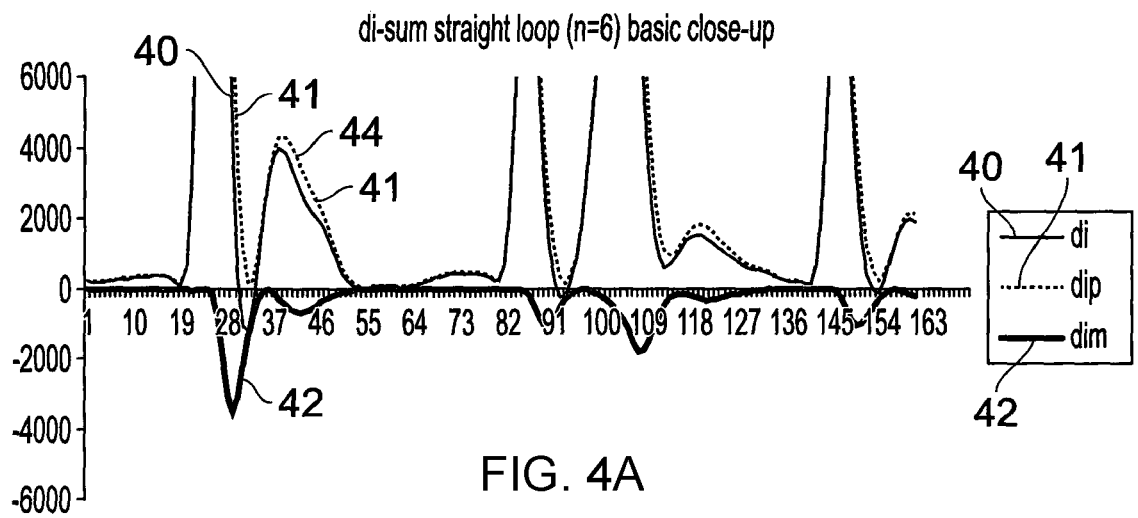
FIGS. 4A-4C show results of measured wave intensities in a rabbit central ear artery.
Figure 4B:
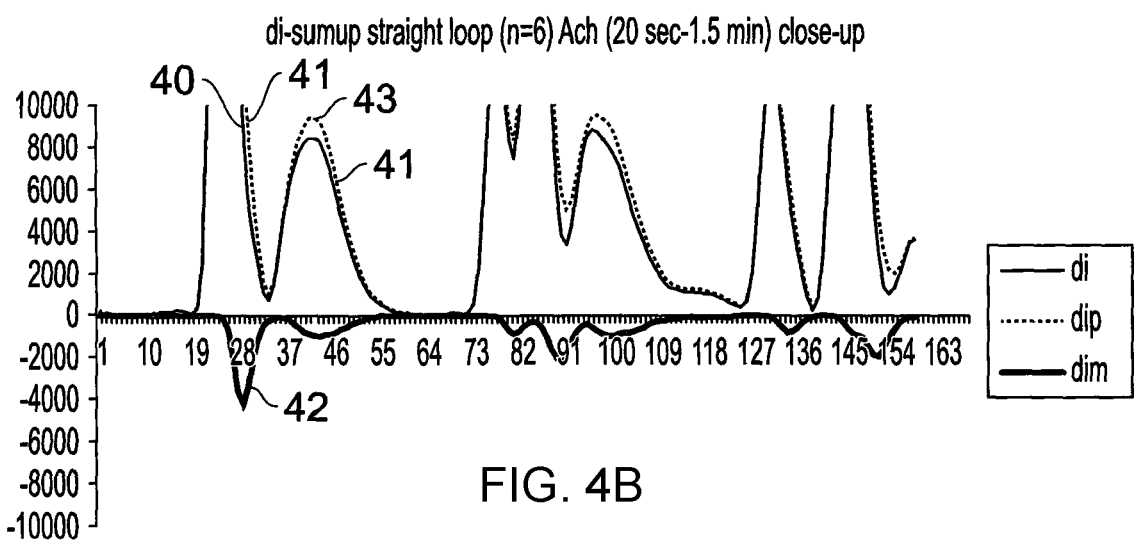
Figure 4C:
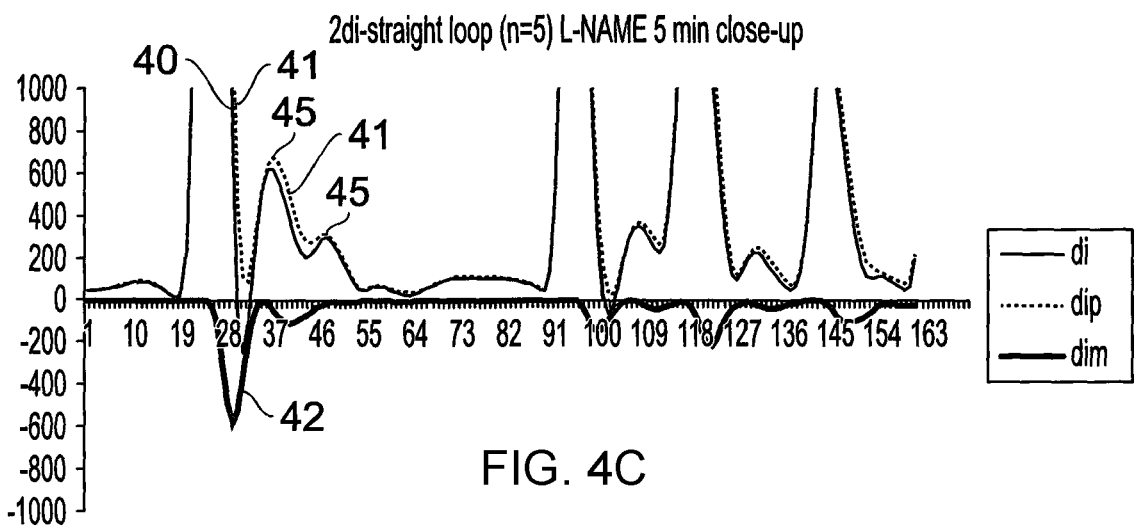

Assessment of endothelial function: it has been noted that the vasodilator nitric oxide (NO) changes the height of the dichrotic notch (a point of inflection between the systolic and diastolic peaks) in the pressure or volume wave. Substances which stimulate NO release, such as acetylcholine (ACh), lower the height of the dichrotic notch. Substances like L-NAME that inhibit NO production raise the height of the dichrotic notch, relative to the overall amplitude of the wave. It has been shown that these changes are quite specific to NO (and the related nitrovasodilators); they do not reflect general influences of vasoactive agents on peripheral tone, blood pressure or heart rate. The effect may be due to altered wave reflections as illustrated in FIGS. 4A-4C. The system 20 may be deployed to determine the effects of NO on wave reflections.

In FIGS. 4A-4C, wave intensities in a rabbit central ear artery are shown. FIG. 4A illustrates wave intensity as a function of time for a baseline condition; FIG. 4B illustrates wave intensity as a function of time after administration of ACh; and FIG. 4C illustrates wave intensity as a function of time after administration of L-NAME. The initial wave (forward compression) has been truncated to more clearly show its reflection from the lower body (line 41, second wave). In FIG. 4B, which illustrates the maximum NO condition, this is a single peak 43. It develops a shoulder 44 in the baseline state (less NO) and a double peak 45 with L-NAME (least NO), indicating that NO is altering these reflections.

The system 20 may be usable to detect heart failure, age-related arterial stiffening and NO-dependent wave reflection in pre-clinical models.

Traditional methods for analysing pulse waves are based on Fourier analysis. The results are in the frequency domain, which makes it hard to relate them to any feature of clinical relevance. Wave Intensity Analysis, in contrast, conceptualises waves as being built up of infinitesimal wavefronts that travel forward or backwards with known intensities at specific times. The breakdown of the pulse wave in this way makes it much easier to relate its features to real cardiac and vascular properties.

WIA may be used in procedures that evaluate the functional significance of coronary stenoses, and hence determine whether intervention is required. It identifies naturally wave-free periods during the cardiac cycle. At such points, the ratio of pressure upstream and downstream of a stenosis can be used to assess the resistance it causes. In a conventional procedure, such periods are not identified and waves may have to be eliminated by administering vasodilating drugs, which is time consuming, expensive, unpleasant for the patient and not feasible in some patient groups. The techniques described herein may provide a non-invasive method without requiring catheterization.

The system may be used for investigating Heart Failure. Curtiss et al [1] compared normal subjects and patients with compensated systolic heart failure. The energy in a re-reflected expansion wave (the X wave) was 80% lower in the patients. Interestingly, the augmentation index based on tonometry—a supposed measure of wave reflections that is not based on WIA—was unchanged. Takaya et al [37] examined patients having chronic heart failure with normal ejection fraction under exercise testing, an accepted method for predicting survival. No transthoracic echocardiography parameters correlated significantly with any exercise parameter, but the intensity of the forward expansion wave (W2) correlated significantly with all exercise parameters, implying that this simple non-invasive measure will better predict outcome. Vriz et al [38] conducted a longitudinal study of patients with heart failure and reduced ejection fraction, comparing wave parameters with echocardiographic indices of left ventricular function. Average follow-up was >3 yr. On stepwise backward multiple regression, only a wave parameter—the intensity of W2—was an independent predictor of outcome. Li and Guo [39] assessed the value of WIA in differentiating non-obstructive hypertrophic cardiomyopathy (NOHCM) from left ventricular hypertrophy secondary to hypertension (LVHSH). They examined the forward going compression (W1) and expansion (W2) waves and an area of negative wave intensity (NA) resulting from peripheral reflections. W2 was lower in NOHCM than in LVHSH and in normal subjects. NA was higher in LVHSH than in NOHCM and normal subjects. The wave intensity parameters differed to a much greater extent than the transthoracic echo parameters: W2 differed 3-fold and NA nearly 2-fold between NOHCM and LVHSH groups, whereas the largest TTE changes were about 40%. Thus WIA is likely to be useful for differentiating between different types of heart failure. Siniawski et al [40] examined patients suffering from end-stage dilative cardiomyopathy and awaiting transplant.

Univariate logistic regression analysis was performed to assess the predictive value of WIA, VO2max, invasively assessed pressures and stroke volume, and echocardiographically-measured ejection fraction. The strongest predictor of events was the 1st peak of wave intensity. Indeed it was only on the basis of the wave parameters that the two groups could be distinguished, again suggesting WIA will predict outcomes.

The clinical need for measuring arterial stiffness, or PWV as a surrogate, is well known—it has frequently been reviewed, and is the subject of consensus or policy documents from expert groups [41,42]. The difficulties and disadvantages of estimating global PWV are presented above. There is much interest in assessing local wall stiffness for clinical purposes and many manufacturers have consequently devised non-invasive methods for doing so. These methods are based on echotracking—they use ultrasound to measure the change in arterial diameter over the cardiac cycle. In order to obtain wall stiffness, it is also necessary to know the local systolic and diastolic pressures. Unfortunately, this brings us back to the problems discussed for applanation tonometry, above. In the method described herein, by contrast, local PWV is obtained from measurements of U and D—pressures are not required—and measurements are feasible from all vessels that can be imaged by ultrasound (including substantial segments of the aorta).

The methods described herein may be used to diagnose endothelial dysfunction through its influence on wave reflections. Endothelial dysfunction—characterised principally by a reduction in NO bioavailability—is a strong risk factor for cardiovascular disease but rarely assessed. That is unfortunate because a number of lifestyle changes have been shown to improve endothelial function. Several pharmacological approaches are also under investigation [43, 44]. It is likely to reflect the technical challenge of measuring such dysfunction. The only method approaching acceptance, at least in a research context, involves inducing flow mediated dilatation: an occlusive cuff is placed around the forearm, inflated above systolic pressure for several minutes, and then released. The increased flow resulting from reactive hyperaemia increases haemodynamic shear stress on the brachial artery endothelium, leading to NO release and dilatation of the vessel. The increase in diameter is assessed from ultrasound images [45]. Although this measure is related to cardiovascular risk [46], many technical issues remain: methods of normalisation for baseline diameter introduce artefacts [47]; cuff position, duration of occlusion and timing of measurement seem critical, and with some the dependence on NO is questionable [48]; there is individual variation in the degree of reactive hyperaemia but normalising by the shear stress appears to cause additional problems [49]; and there is great operator dependence that needs to be minimised by holding the probe with a micrometer-adjustable stereotaxic apparatus [48]. In the methods described herein, endothelial function could be assessed from the effect of NO on pulse waves rather than solely on diameter.

Current ultrafast ultrasound systems can resolve down to 100 microns, which is more than adequate for obtaining sufficient accuracy in the dD term and the resolution in velocity is <1% of peak velocity and leads to acceptably small errors in dU. Furthermore, the speed of such system (>1000 frames/s) is sufficient to "freeze" the motion of vessels that move during the cardiac cycle. To date, signal-to-noise ratios have been acceptable and microbubble contrast agents could be used to improve them further, for example by distinguishing non-linear signals emitted by the microbubbles and linear signals emitted by the tissue.

The methods of determining wave speed and/or determining wave intensity generally have application in any non-rigid fluid conduit system, particularly within a system exhibiting elastic behaviour in the walls in at least part of the system. The expression 'conduit' encompasses pipes and tubes which may have varying diameters and cross-sectional profiles, which may be branching and which may have chambers connected thereto. Generally, the techniques described could be applied in any elastic walled fluid conduit which has sufficient transparency to ultrasound to enable the tracking of objects within a flow of fluid within the conduit. The techniques could generally be applicable to a system where compression/decompression waves may arise within the fluid conduit, e.g. from the operation of valves within the system.

The equations used as described above, to determine wave speed, wave intensity, and/or wave energy, can be modified for greater accuracy to take into account other measurable properties of the system such as viscosity of the fluid medium (e.g. blood), viscoelasticity of the conduit walls and other non-linear effects. In one method [57], this may be achieved by making additional measurements of D or U (or equivalently additional measurements of A or Q) at a second site along the conduit. The equations used to determine wave speed could be modified to take account of reflections, e.g. using a correction factor as derived by P Segers et al [27].

Wave intensity analysis techniques such as those used in this disclosure can be improved by subtracting "windkessel" effects, i.e. subtracting the pressure that is caused by the elastic vessels being pumped full of blood, and not by waves [56].

Other methods for calculation of wave speed

Using pressure and velocity, wave speed is conventionally calculated as $$c=(1/rho)(dP/dU)$$

where rho ($\rho$) is fluid density. This method and those exemplified earlier in this document may be used in early systole, when reflections can be considered to be negligible.

Wave speed can also be calculated when waves are not unidirectional using the "sum-of-squares" method [54]:

$$c=(1/rho)[(\Sigma dP^2)/(\Sigma dU^2)]^{0.5}$$

where $\Sigma$ is the sum over the cardiac cycle.

It may be possible to convert this to an equation based on A (cross-sectional area) and D (conduit diameter), such as $$c=0.5[(\Sigma dU^2)/\Sigma d\ln D^2)]^{0.5}$$

thereby also falling within the general ambit of a function of (i) the change in fluid velocity at the longitudinal position as a function of time and (ii) the change in the conduit diameter as a function of time.

Other embodiments are intentionally within the scope of the accompanying claims.

LIST OF REFERENCES

[1] Curtis, S L et al. Am J Physiol Heart Circ Physiol 2007, 293:H557. [2] Sugawara, M et al. Med Biol Eng Comput 2009, 47:197. [3] Avolio, A P et al. Circulation 1985, 1985:202. [4] Laurent, S et al. Eur Heart J 2006, 27:2588. [5] van Popele, N M et al. Stroke 2001, 32:454. [6] Manisty C et al, J Am Coll Cardiol 2010, 56:24. [7] Manisty, C H et al. Hypertension 2009, 54:724. [8] Bradlow, W M et al. J. Magn. Reson. Imaging 2007, 25:974. [9] Taviani, V et al. Magn Reson Med 2011, 65:261. [10] O'Rourke, M F et al. Am J Hypertens 2002, 15:426. [11] Tsai, W-C et al. Am J Hypertens 2013, 26:770. [12] Khir A W et al, J Biomech 2001, 34; 1145. [13] Parker, K H et al. Heart Vessels 1988, 4:241. 14 http://www.bg.ic.ac.uk/research/k.parker/wave_intensity_web/welcome.html [15] Sens S et al. J Am Coll Cardiol. 2012, 59:1392. [16] Beulen, B W et al. Ultrasound Med Biol 2011, 37:788. [17] Feng, J et al. J Biomech 2010, 43:455. [18] Biglino G et al. Int J Artif Organs. 2012, 35:15. [19] Kolyva C et al. Artif Organs. 2012, 36:E62. [20] Li, Y et al. Proc IEEE Eng Med Biol, 2010, 2010: 5153. [21] Poelma, C et al. Exp Fluids 2011, 2011:777. [22] Poelma, C et al. Eur J Mech B/Fluids 2012, 35:70. [23] Zhou, B et al. Ultrasound Med Biol 2013, 39:1672. [24] Poelma C, Fraser K H. Meas Sci & Tech 2013, 24:115701. [25] Tanter M, Fink M, IEEE Trans UFFC, 2014, 61: 102. [26] Leow C H et al. Ultrasound Med Biol. 2015, 41:2913 [27] Segers P et al. Physiol Meas. 2014, 35: 847. [28] Sardarlou, M. Non-invasive Assessment of Arterial Wavespeed and Endothelial Function, PhD Thesis, Imperial College London 2013. [29] Li Y, Khir A W. J Biomech. 2011, 44:1393. [30] Alastruey J et al. Int J Numer Method Biomed Eng. 2014, 30:249 [31] Mehrad, H et al. Ultrasound Med Biol 2012, 38:1391. [32] Lee, S C et al. J Am Coll Cardiol Img 2010, 3:1265. [33] Arnolda, L et al. Cardiovasc Res 1985, 19:378. [34] Weinberg P D et al. Br J Pharmacol 2001, 133:361. [35] Nier, B A et al. Exp Physiol 2008, 93:503. [36] Morikawa Y. Nature 1967, 213 (5078):841. [37] Takaya Y et al. Heart Vessels. 2013, 28:179. [38] Vriz O et al. Int J Cardiovasc Imaging. 2015, 31:1369. [39] Li Y, Guo L J Clin Ultrasound 2013, 41:151. [40] Siniawski H et al. J Basic Appl Physics 2013, 2:95. [41] Townsend R R et al. Hypertension. 2015, 66:698. [42] Laurent s et al. Eur Heart J. 2006, 27:2588. [43] Wang Q et al. Evid Based Complement Alternat Med. 2014, 2014:850312. [44] Kövamees O et al. J Intern Med. 2015 doi: 10.1111/joim.12461. [45] Celermajer D S et al Lancet 1992, 340:1111. [46] Xu Y et al. Eur Heart J Cardiovasc Imaging. 2014,15:736. [47] Atkinson G, Batterham A M. Vasc Med. 2013, 18:354. [48] Al-Qaisi M et al. Vasc Health Risk Manag. 2008, 4:647. [49] Thijssen D H et al. Am J Physiol Heart Circ Physiol. 2009, 296:H57. [50] Yildiz Y O et al. Ultrasound Med Biol. 2015, 41:1938. [51] Cheung W K et al. Ultrasound Med Biol. 2015, 41:1876. [52] Alastruey J, Hunt A A, Weinberg P D. Novel wave intensity analysis of arterial pulse wave propagation accounting for peripheral reflections. Int J Numer Method Biomed Eng. 2014; 30: 249-279. [53] Vulliérnoz S, Stergiopulos N, and Meuli R. Estimation of local aortic elastic properties with MRI. Magn Reson Med. 2002; 47:649-654. [54] Davies J, Whinnett Z, Francis D, Willson K, Foale R, Malik I, Hughes A, Parker K, Mayet J. Use of simultaneous pressure and velocity measurements to estimate arterial wave speed at a single site in humans. Am J Physiol Heart Circ Physiol, 2006; 290:H878-H885. [55] Rabben S I, Stergiopulos N, Hellevik L R, Smiseth O A, Slørdahl S, Urheim S, Angelsen B. An ultrasound-based method for determining pulse wave velocity in superficial arteries. J Biomech. 2004; 37:1615-1622. [56] JJ Wang et al, Am J Physiol Heart Circ Physiol 2003; 284: H1358-H1368. [57] Stergiopulos N, Tardy Y, Meister J J. Nonlinear separation of forward and backward running waves in elastic conduits. J Biomech. 1993; 2:201-209.

The invention claimed is:

1. A method of determining a measure of wave speed in a fluid flowing through a fluid conduit, the method comprising:
   using ultrasound measurements to determine the conduit diameter or conduit cross-sectional area, as a function of time, at a longitudinal position of the conduit;
   using ultrasound measurements to determine fluid velocity, as a function of time, in a volume element at said longitudinal position of the conduit, the ultrasound measurement to determine fluid velocity being effected by tracking objects within the fluid flow in successive frames sampling the volume element, and obtaining displacement vectors for the objects, in which the objects being tracked comprise red blood cells, white blood cells, or platelets;
   determining a wave speed from a function of (i) the change in fluid velocity at the longitudinal position as a function of time and (ii) the change in the conduit diameter or conduit cross-sectional area, as a function of time.

2. The method of claim 1 in which the wave speed is determined from a ratio of the change in fluid velocity at the longitudinal position as a function of time and the change in a logarithmic function of the conduit diameter as a function of time.

3. The method of claim 2 in which the wave speed is determined from a ratio of a change in fluid velocity at the longitudinal position within a time interval and a corresponding change in a logarithmic function of the conduit diameter within the same time interval.

4. The method of claim 1 in which the wave speed is determined from the change in fluid velocity at the longitudinal position within a time interval and a corresponding change in the conduit diameter within the same time interval.

5. The method of claim 1 in which the fluid velocity is determined using imaging velocimetry.

6. The method of claim 1 in which the ultrasound measurements for determining fluid velocity comprise a series of B-mode images or B-mode RF data, and obtaining displacement vectors comprises correlating the locations of the tracked objects in successive frames of the B-mode images or B-mode RF data.

7. The method of claim 1 in which the ultrasound measurements for determining conduit diameter and fluid velocity are both derived from a common ultrasound transducer head.

8. The method of claim 7 in which the common transducer head is directed orthogonally to a fluid flow axis of the fluid flow conduit.

9. The method of claim 7 in which the ultrasound measurements for determining conduit diameter or conduit cross-sectional area, and fluid velocity are both derived from common ultrasound excitation and response signals.

10. The method of claim 1 in which the wave speed, c, is determined according to the equation $c=0.5(dU/d\ln D)$, where $dU$ is a change in the fluid velocity as a function of time and $d\ln D$ is a change in the natural logarithm of D as a function of time.

11. The method of claim 1 in which the fluid conduit comprises a part of the human or animal circulatory system.

12. The method of claim 11 further including repeating the ultrasound measurements and determining a wave speed at multiple times during a cardiac cycle and correlating the measurement of wave speed with time within the cardiac cycle.

13. The method of claim 1 further including determining a measure of fluid conduit wall elasticity or distensibility at the volume element, from the wave speed.

14. The method of claim 1 in which the wave speed, c, is determined according to the equation c=AdU/dA or c=dU/dlnA, where A is the cross-sectional area, dA is the change in cross-sectional area as a function of time, dU is the change in the fluid velocity as a function of time, and dlnA is the change in the natural logarithm of A as a function of time.

15. A method of determining a measure of wave speed in a fluid flowing through a fluid conduit, the method comprising:
   using ultrasound measurements to determine the conduit diameter, as a function of time, at a longitudinal position of the conduit;
   using ultrasound measurements to determine fluid velocity, as a function of time, in a volume element at said longitudinal position of the conduit, the ultrasound measurement to determine fluid velocity being effected by tracking objects within the fluid flow in successive frames sampling the volume element, and obtaining displacement vectors for the objects, in which the objects being tracked comprise red blood cells, white blood cells, or platelets;
   determining a change in flow rate through the conduit based on the fluid velocity measurements and the conduit diameter measurements;
   determining a change in cross-sectional area of the conduit based on the conduit diameter measurements; and
   determining a wave speed from a ratio of the change in flow rate at the longitudinal position as a function of time and the change in conduit cross-sectional area as a function of time.

16. The method of claim 15 in which the fluid velocity is determined using imaging velocimetry.

17. The method of claim 15 in which the ultrasound measurements for determining fluid velocity comprise a series of B-mode images or B-mode RF data, and obtaining displacement vectors comprises correlating the locations of the tracked objects in successive frames of the B-mode images or B-mode RF data.

18. The method of claim 15 in which the ultrasound measurements for determining conduit diameter and fluid velocity are both derived from a common ultrasound transducer head.

19. The method of claim 18 in which the common transducer head is directed orthogonally to the fluid flow axis of the fluid flow conduit.

20. The method of claim 19 in which the ultrasound measurements for determining conduit diameter and fluid velocity are both derived from common ultrasound excitation and response signals.

21. The method of claim 15 in which the wave speed, c, is determined according to the equation c=dQ/dA), where dQ is a change in the fluid flow rate and dA is a change in the cross-sectional area of the conduit.

22. The method of claim 15 in which the fluid conduit comprises a part of the human or animal circulatory system.

23. The method of claim 22 further including repeating the ultrasound measurements and determining a wave speed at multiple times during a cardiac cycle and correlating the measurement of wave speed with time within the cardiac cycle.

24. The method of claim 15 further including determining a measure of fluid conduit wall elasticity or distensibility at the volume element, from the wave speed.

25. An apparatus for determining a measure of wave speed in a fluid conduit, comprising:
   an analysis module configured to perform the steps of claim 1.

26. An apparatus for determining a measure of wave speed in a fluid conduit, comprising:
   an analysis module configured to perform the steps of claim 15.

* * * * *